United States Patent [19]
Roussouly et al.

[11] Patent Number: 5,810,817
[45] Date of Patent: Sep. 22, 1998

[54] SPINAL THERAPY APPARATUS

[76] Inventors: Pierre Roussouly, 53, avenue Barthélémy Buyer, 69005 Lyon; Gilbert Taglang, 9, rue Paul Verlaine, 67370 Griesheim sur Souffel; Arsène Grosse, 5, rue des Fougères, 67400 Illkirch-Graffenstaden; Daniel Chopin, 65 avenue du Touquet-Stella, 62780 Cucq, all of France

[21] Appl. No.: 863,066

[22] Filed: May 23, 1997

Related U.S. Application Data

[63] Continuation of Ser. No. 351,251, filed as PCT/FR93/00605, Jun. 18, 1993, published as WO94/00062, Jan. 6, 1994, abandoned.

[30] Foreign Application Priority Data

Jun. 19, 1992 [FR] France ................................ 92 07504

[51] Int. Cl.⁶ .................................................. A61B 17/70
[52] U.S. Cl. .................................. 606/61; 606/73; 606/72
[58] Field of Search ................................. 606/61, 60, 72, 606/73, 69, 70, 71; 623/17

[56] References Cited

U.S. PATENT DOCUMENTS 4,648,388  3/1987  Steffee .
4,773,402  9/1988  Asher et al. .
4,987,892  1/1991  Krag et al. .
5,084,049  1/1992  Asher et al. .............................. 606/61
5,176,679  1/1993  Lin ............................................. 606/61
5,380,325  1/1995  Lahille et al. ............................ 606/61

FOREIGN PATENT DOCUMENTS 383992  8/1990  European Pat. Off. .
408489  1/1991  European Pat. Off. .
2615095  11/1988  France .
87/01026  2/1987  WIPO .

Primary Examiner—Guy V. Tucker
Attorney, Agent, or Firm—William H. Eilberg

[57] ABSTRACT

An apparatus including vertebral anchoring elements, such as a bone screw (1) or a hook (2), with a threaded cylindrical portion (5) and a locking plate (7). A nut (8) may be screwed onto the threaded cylindrical portion (5) to tighten the tightening portion of a slide (4) on a rigid connecting rod (3) with a circular cross-section. The rod (3), the slide (4) and the anchoring element (1,2) may be sufficiently rigidly connected by means of non-slip projections on the engaged side of the locking plate (7), on the corresponding side of the slide (4), and on the surface thereof which surrounds the rod (3). The stiffness of the apparatus may thus be enhanced, so that improved support of the vertebrae and easier fitting and adjustment of the apparatus may be achieved.

21 Claims, 12 Drawing Sheets

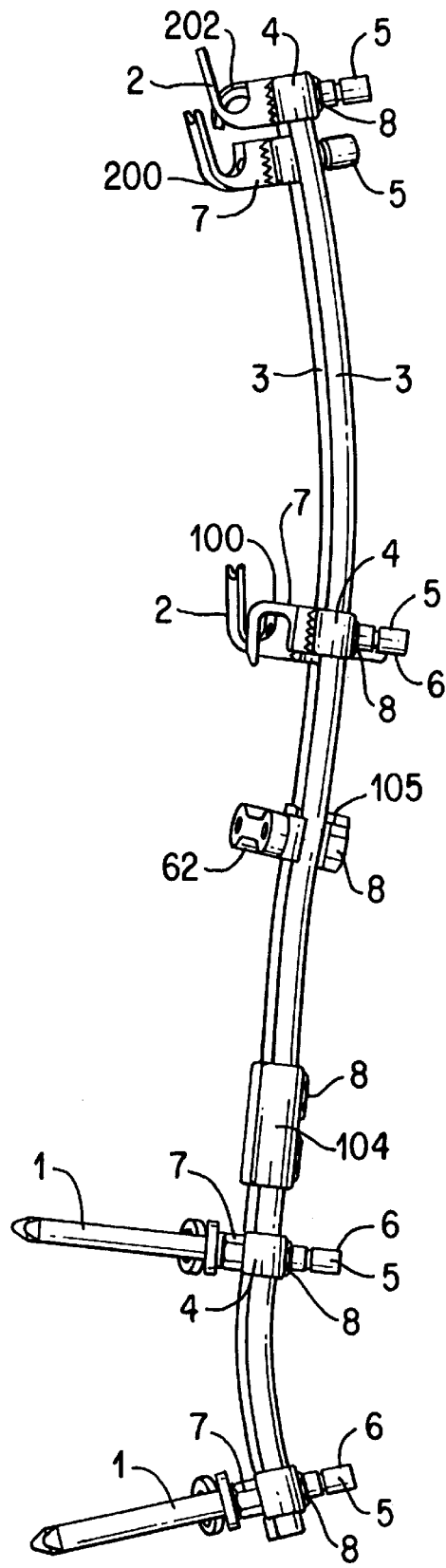
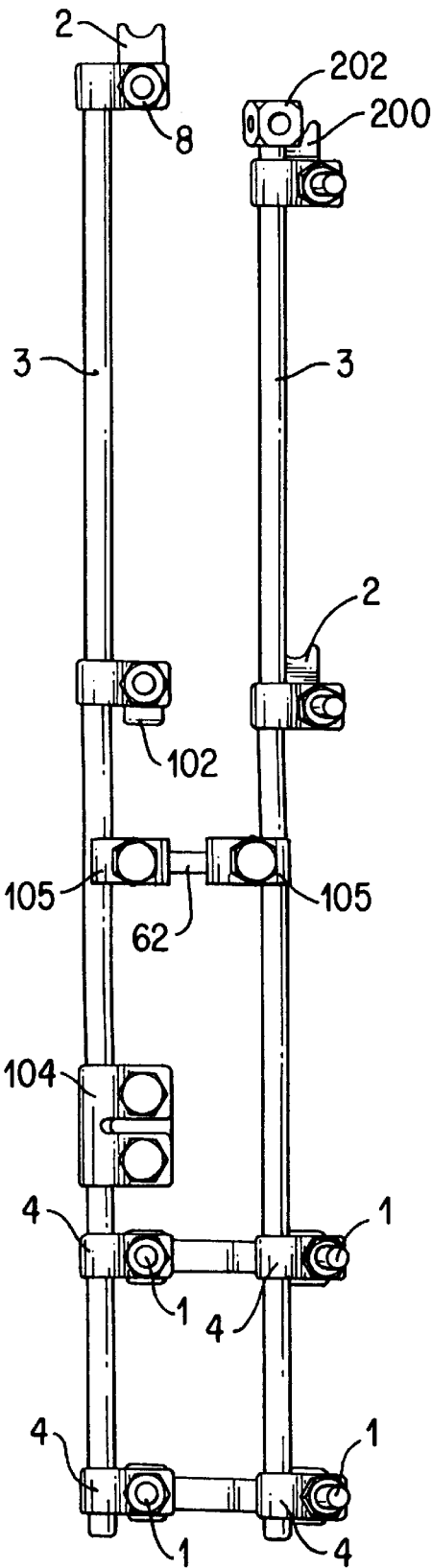
FIG. 1
FIG. 2

SPINAL THERAPY APPARATUS

This application is a continuation of application Ser. No. 08/351,251, filed as PCT/FR93/00605, Jun. 18, 1993 published as WO94/00062, Jan. 6, 1994, now abandoned.

FIELD OF THE INVENTION

The present invention concerns a spinal therapy device for treating a spinal column having an abnormal deformation as a result of degeneration or trauma.

The prior art includes many devices for treating vertebral arthroses or fractures or for correcting deformation of the vertebral column such as scoliosis, lordosis and kyphosis.

For example, document U.S. Pat. No. 4,648,388 describes a spinal therapy device having vertebral anchoring elements, a circular cross-section fastening rod with a smooth outside surface and connecting slides for connecting the anchoring elements to the fastening rod. The anchoring elements are screws with three main parts, a helically threaded first end part adapted to penetrate and to be held in the bone, a smaller diameter smooth cylindrical intermediate part, and a helically threaded second end part adapted to have a clamping nut screwed onto it. The connecting slides have a clamping part shaped to surround a section of the fastening rod and a connection part projecting laterally with two corresponding holes through which the anchor screw passes. The screw is first screwed into the bone, after which the connecting slide is fitted to the cylindrical intermediate part of the screw, and finally the clamping nut is screwed onto the second threaded part of the screw to press the connecting slide against a vertebra and at the same time to clamp the connecting slide around the fastening rod.

A device of this kind is designed to maintain an appropriate curvature of the spinal column. However, this device does not provide sufficient mechanical support. In particular, the direct bearing engagement of the slide on a vertebra rules out any possibility of effective clamping because of the low mechanical strength in compression of the vertebra. Also, fitting the device to a spinal column sometimes requires the simultaneous use of two tools, for example to prevent rotation of the screw when screwing on or unscrewing the nut. Notches along the fastening rod reduce its mechanical strength and increase its flexibility. Also, this device is not compatible with three-dimensional reduction of the upper part of the spinal column, where screws cannot be inserted. Most importantly, the clamping force of the nut substantially increases the traction loading on the screw, combining with the forces retaining the fastening rod, which reduces commensurately the mechanical strength of the anchorage and promotes necrosis of the bone around the screw.

Document EP-A-0 408 489 describes a device for joining two vertebrae together by means of two double-threaded pedicle screws and two slides linked by a screwthreaded rod so that the distance between them can be adjusted. The screw has spherical bearing surfaces for adjusting the inclination relative to the slide, the tightening of a clamping nut onto the screwthreaded part of the screw preventing rotation. This device, which would appear suitable for adjusting the spacing of two consecutive vertebrae, is totally unsuited to supporting more than two vertebrae and there is no teaching as to the problem of insufficient mechanical retention of smooth connecting rods.

SUMMARY OF THE INVENTION

The problem to which the present invention is addressed is that of designing a new spinal therapy device having a smooth fastening rod and connecting slides for anchoring elements which is much more effective in fastening together the vertebrae and makes it easier to fit the device and to adjust the position of the component parts of the device relative to each other in three dimensions.

The invention arises out of the observation that supporting and positioning defects of prior art devices, combined with the relative complexity of fitting and adjusting them, are due to the possibility of pivoting either between the connecting slides and the fastening rod or between the connecting slides and the respective anchoring element. High rotation torques are generated on reducing deformation of the spinal column and consequently during supporting of the treated spinal column and the prior art devices are not able to withstand reliably these high torques.

For this, the device of the present invention comprises:
anchoring elements adapted to be anchored in the vertebrae and having a screwthreaded cylindrical part onto which a clamping nut is screwed,
at least one circular cross-section fastening rod having a smooth outside surface,
connecting slides for connecting anchoring elements to the fastening rod, the connecting slides having a clamping part and a connecting part, the clamping part having inside surfaces shaped to surround a section of the fastening rod and being deformable for selectively clamping them to and releasing them from the fastening rod, the connecting part having a first branch and a second branch extending laterally and parallel to each other from two lips of a longitudinal slot in the clamping part, said branches of the connecting part having corresponding through-holes for receiving an anchoring element for clamping the branches together and thereby clamping the clamping part and for receiving the screwthreaded cylindrical part of an anchoring element, characterised in that:
the anchoring elements include a locking plate with a bearing surface generally perpendicular to the axis of the screwthreaded cylindrical part and extending from its base,
the bearing surface of the locking plate includes first non-slip projections,
the corresponding first contact surface of the first branch of the connecting part, adapted to bear against the bearing surface of the anchoring element, includes corresponding first non-slip projections to oppose any rotation and any lateral displacement of the connecting slide relative to the anchoring element after clamping of the nut against the opposite second contact surface of the second branch of the connecting part.

The inside surfaces of the clamping part preferably include non-slip projections providing discontinuous bearing engagement opposing rotation of the connecting slide around the fastening rod after clamping of the clamping member.

The non-slip projections are very effective in opposing rotation or sliding between the slides and the fastening rod and simultaneously between the slides and the anchoring elements, which movements occur immediately tightening of the clamping nuts is started. At the same time, the non-slip projections associated with the locking plate prevent rotation of the anchoring element during tightening of the nut even when the anchoring element is in the form of a bone screw, with the result that only one tool is needed to tighten the nut.

These arrangements also enable precise adjustment of the relative position of the components, including accurate adjustment of the angular position of the connecting slides on the fastening rod and accurate adjustment of the angular position of the connecting slides on the anchoring elements, by virtue of a locking effect before complete tightening.

By way of anchoring elements the device may include one or more double-threaded bone screws on either side of an intermediate locking plate with non-slip projections, one or more hooks whose rear wall provides a locking plate and includes non-slip projections, and possibly bearing plates shaped to match the specific morphology of certain areas of the spinal column and including non-slip projections.

BRIEF DESCRIPTION OF THE DRAWINGS

Further objects, features and advantages of the present invention will emerge from the following description of specific embodiments of the invention given with reference to the appended drawings, in which:

FIGS. 1 and 2 are respectively side and front views of one embodiment of a device in accordance with the invention;

DESCRIPTION OF THE PREFERRED EMBODIMENTS

Figure 3:
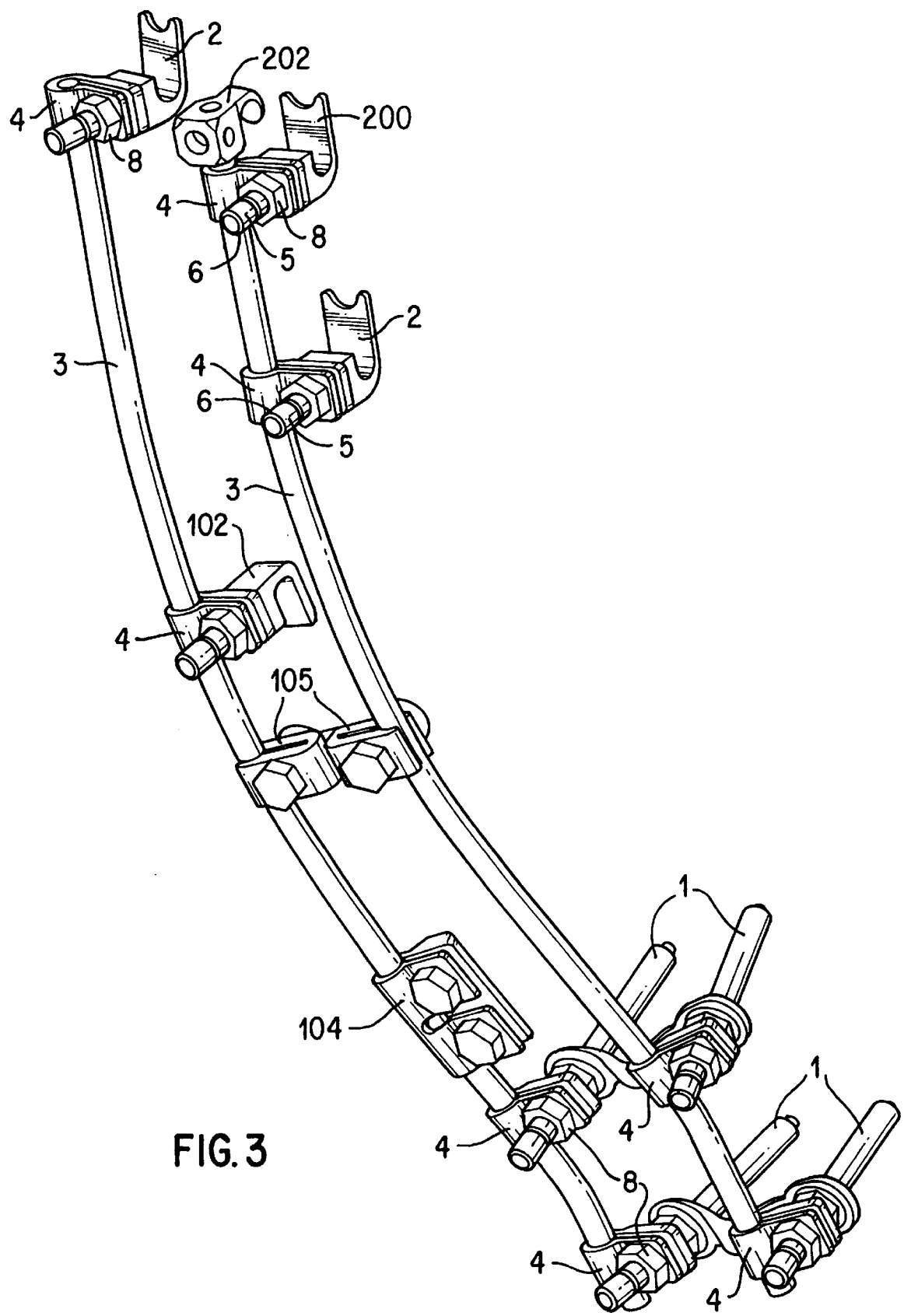
FIG. 3 is a perspective view of the device from FIGS. 1 and 2.

The device shown in FIGS. 1 to 3 includes anchoring elements such as bone screws 1 or hooks 2, 102, 202, fastening rods 3 and connecting slides 4 between each anchoring element and the fastening rod 3.

The fastening rods 3 of the device of the invention are smooth rods with a circular cross-section. The material and the cross-section are chosen for optimum elasticity, matched to the loads encountered in use, and such that the rod can be curved to the required shape for the part of the vertebral column to be treated.

Each anchoring element, bone screw, hook or bearing plate is in one piece with a screwthreaded cylindrical part 5 having an exterior screwthread 6 and includes a locking plate 7 limiting the clamping of a nut 8 onto the exterior screwthread 6.

Figure 4:
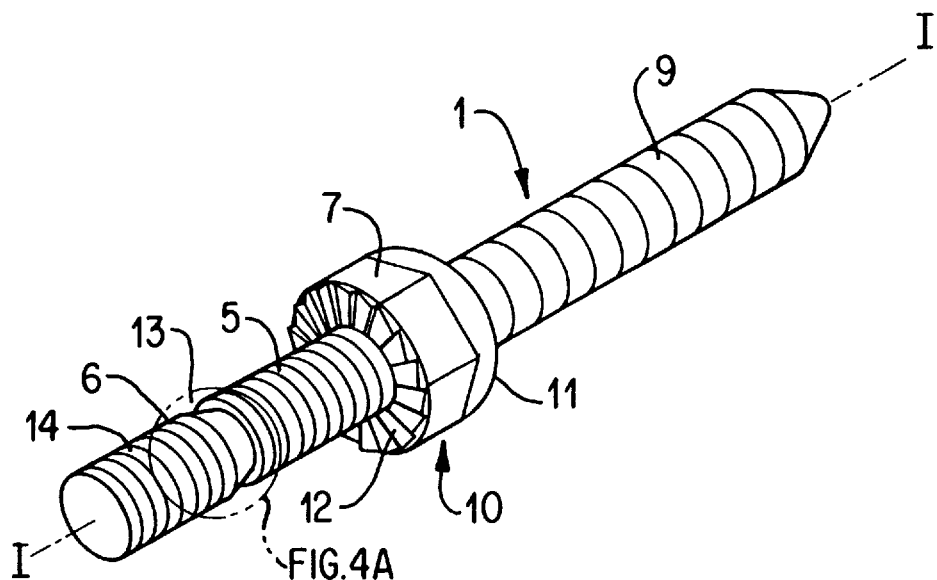
FIG. 4 is a perspective view of a bone screw that can be used as an anchoring element in implementation of the invention.
Figure 4A:
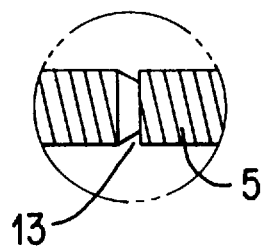

In the FIG. 4 embodiment the anchoring element is a double-threaded bone screw 1, the screwthreaded cylindrical part 5 with the exterior screwthread 6 constituting the first screwthread, a screwthreaded coaxial cylindrical second part 9 constituting a second screwthread adapted to be screwed into the bone, the locking plate 7 constituting an intermediate part of greater cross-section between the two screwthreaded parts 5 and 9. The locking plate 7 advantageously has a faceted peripheral surface 10 with six flats, an abutment surface 11 merging with the screwthreaded cylindrical second part 9 and adapted to bear against the bone of the vertebra, and a bearing surface 12 generally perpendicular to the axis I—I of the screwthreaded cylindrical part 5 and extending from its base.

The bearing surface 12 of the locking plate 7 includes first non-slip projections. For example, these first non-slip projections can be a granular surface or (preferably) radial ribs distributed over the bearing surface from the base of the screwthreaded cylindrical part 5. The screwthreaded cylindrical part 5 includes at least one intermediate annular groove 13 constituting an area of weakness to facilitate separation of the excess part 14 after screwing a nut onto the screwthreaded cylindrical part 5. The groove 13 advantageously has a sawtooth cross-section, the bottom of the groove being adjacent the remaining part of the screwthreaded cylindrical part 5.

Figure 5:
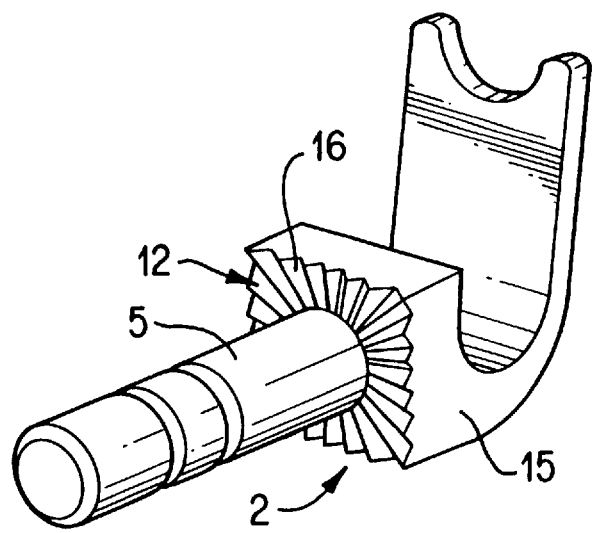
FIG. 5 is a perspective view showing a pedicle hook which can be used as an anchoring element in implementation of the invention.

In the FIG. 5 embodiment the anchoring element is a pedicle hook 2 adapted to be hooked over the pedicle of a vertebra. The hook 2 has a hook body 15, curved as shown in the figure, and a rear wall or bearing surface 12 with which the screwthreaded cylindrical part 5 merges. The bearing surface 12 is generally perpendicular to the axis of the screwthreaded cylindrical part 5 and provides a locking plate. As in the case of the pedicle screw in FIG. 4, the bearing surface 12 includes first non-slip projections such as radial ribs 16.

Figure 6:
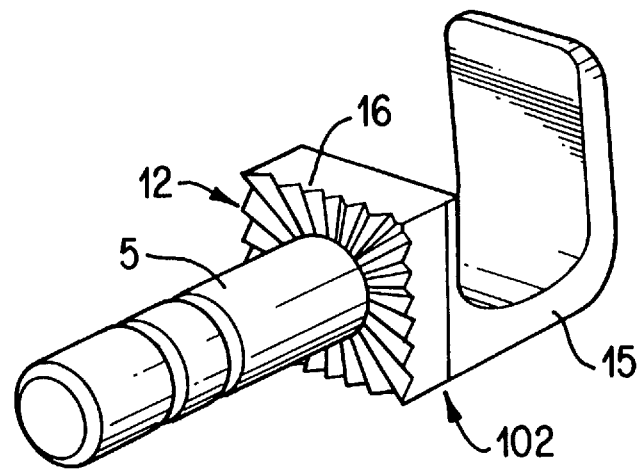
FIG. 6 is a perspective view of a lamina hook that can be used as an anchoring element in implementation of the invention.

The FIG. 6 embodiment shows an anchoring element in the form of a lamina hook 102 shaped to be hooked over a vertebra lamina. The hook body 15 is slightly different to that in FIG. 5, the other parts being identical, in particular the bearing surface 12 with the radial ribs 16 around the base of the screwthreaded cylindrical part 5.

In both the FIG. 5 and FIG. 6 embodiments the bearing surfaces 12 of the hook body 15 constitute the locking plate of the anchoring element to limit clamping of a nut onto the screwthreaded cylindrical part 5.

Figure 7:
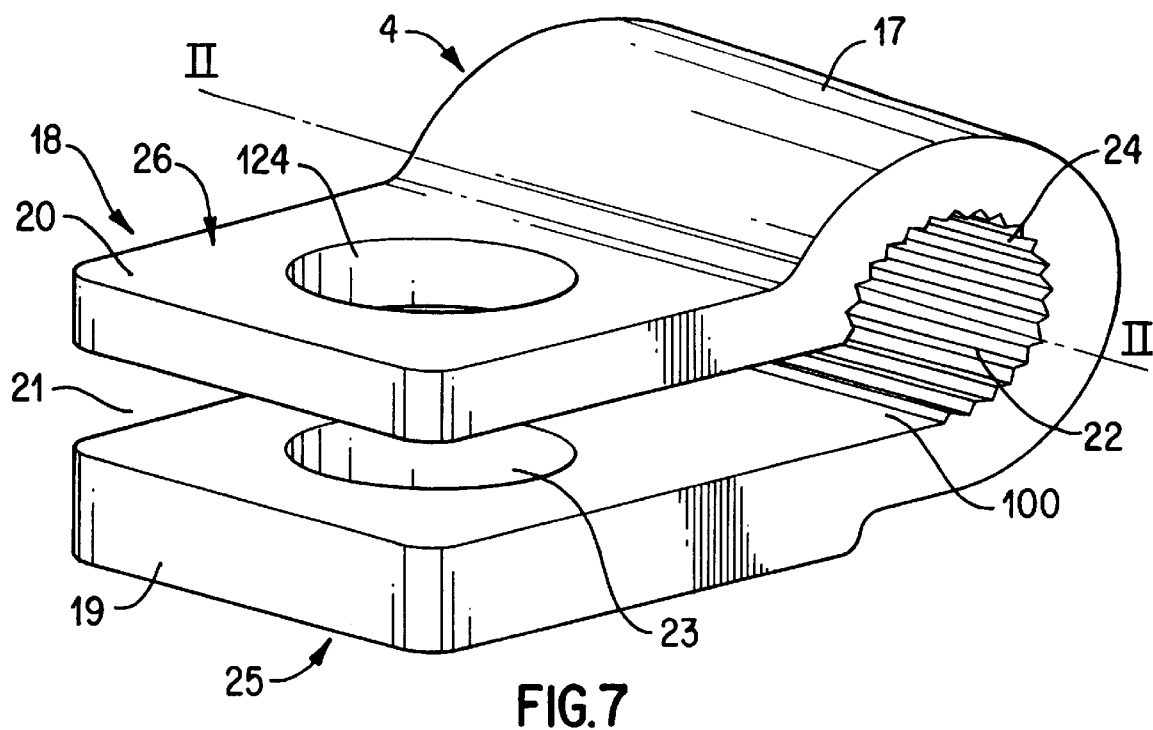
FIG. 7 is a perspective view of a connecting slide in a first embodiment of the invention.
Figure 8:
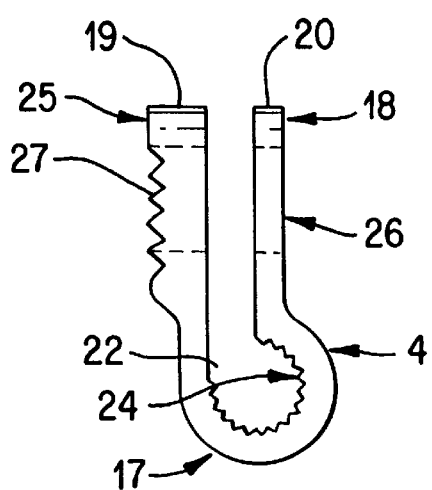
FIGS. 8 and 9 are respectively side and bottom views of the connecting slide from FIG. 7.
Figure 9:
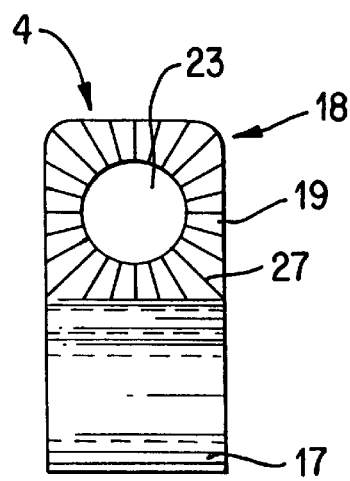

In the embodiment of FIGS. 7 to 9 the connecting slide 4 of the invention has a clamping part 17 and a connecting part 18.

The connecting part 18 has a first branch 19 and a second branch 20 which are generally flat with a gap 21 between them in the free state; they extend laterally and parallel to each other from two lips of a longitudinal slot 100 in the generally cylindrical clamping part 17 by which they are joined together. The clamping part 17 has a generally cylindrical inside surface 22 defining a passage shaped to surround a section of the fastening rod 3. The clamping part 17 is deformable so that it can be clamped selectively onto tie fastening rod 3 or released therefrom.

Each of the branches 19 and 20 includes a respective through-hole 23 and 124, coaxial with each other and having their common axis perpendicular to the axis of the inside surface 22 of the clamping part 17. The through-holes 23 and 124 are shaped to receive the screwthreaded cylindrical part 5 of an anchoring element. With substantial advantage the hole 124 could be replaced by a slot enabling relative inclination of the slide during its fitting to an anchoring element.

When the screwthreaded cylindrical part 5 of an anchoring element 1, 2, 102 or 202 is inserted into the holes 23 and 124 of a slide 4 and the nut 8 is tightened until the two branches 19 and 20 are forced towards each other, the clamping part 17 is deformed and the diameter of the cylindrical inside surface 22 decreases so that it is clamped onto the rod 3. In this embodiment the anchoring element is therefore also a clamping member.

The inside surface 22 of the clamping part 17 has second non-slip projections opposing rotation of the connecting slide 4 around the fastening rod 3 after tightening the clamping member. For example, the second non-slip projections are advantageously longitudinal ribs 24, preferably having a triangular transverse cross-section, forming a discontinuous contact surface on the fastening rod 3.

At the time of use, the first contact surface 25 of the first branch 19 of the connecting part 18 bears against the bearing surface 12 of an anchoring element. This first contact surface 25 has also corresponding first non-slip projections similar to those on the bearing surface 12 of the anchoring element, in order to oppose any rotation and any lateral displacement of the connecting slide 4 relative to the anchoring element after tightening of the nut 8 against the opposite contact surface 26 of the second branch 20 of the connecting part 18.

The first non-slip projections on the surface 25 are radial ribs 27, for example, as shown in FIGS. 8 and 9, surrounding the hole 23 which can advantageously have a shape complementary to that of the radial ribs of the anchoring elements. The slide can therefore be locked in various angular positions to the anchoring element and this locking prevents subsequent unintentional loosening of the nuts 8.

Note that in the embodiment shown the first connecting branch 19 incorporating the first contact surface 25 is offset outwardly relative to the axis II—II of the clamping part 17 or the axis of the interior cylindrical surface 22. Accordingly, the fastening rod 3 is slightly offset from the vertebra.

Figure 10:
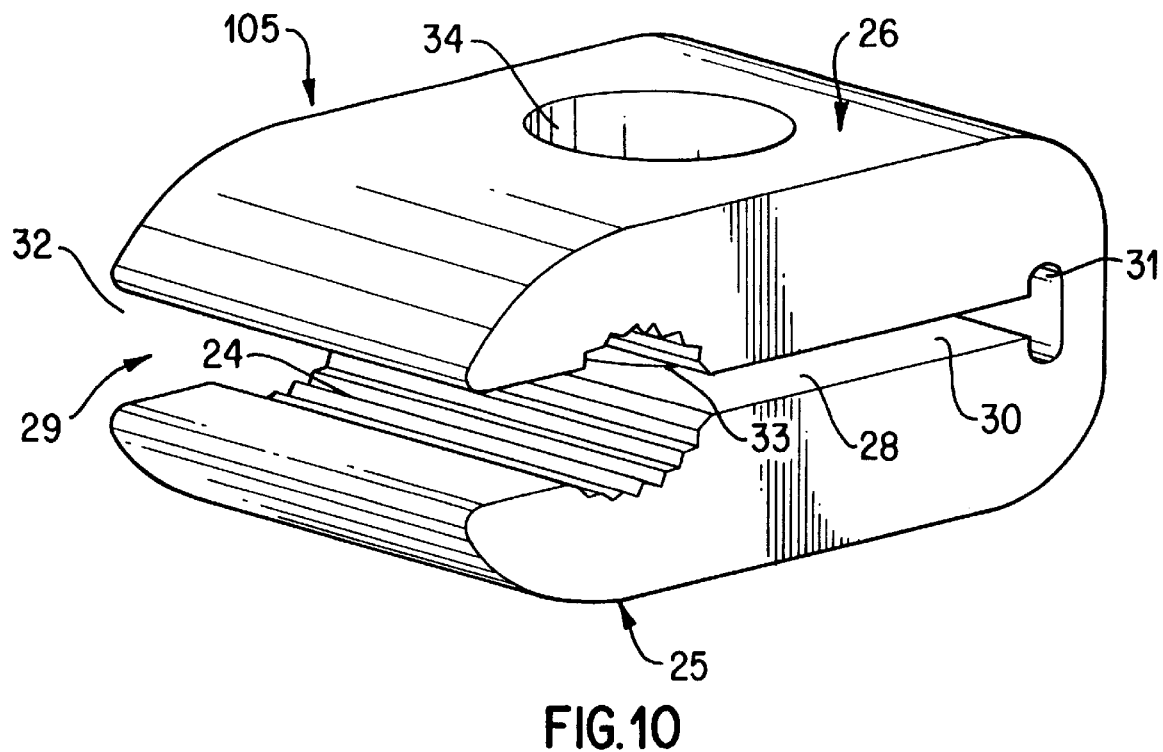
FIG. 10 is a perspective view of a connecting slide in a second embodiment of the invention.
Figure 11:
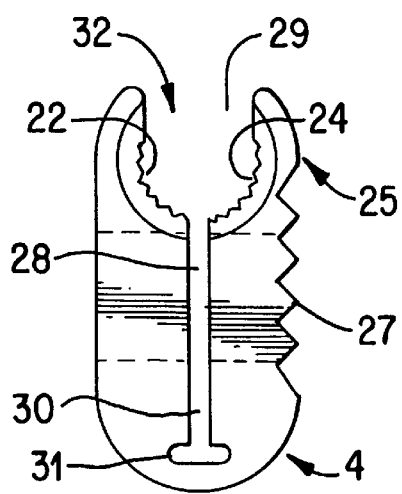
FIGS. 11 and 12 show the connecting slide from FIG. 10 respectively in side view and from below.
Figure 12:
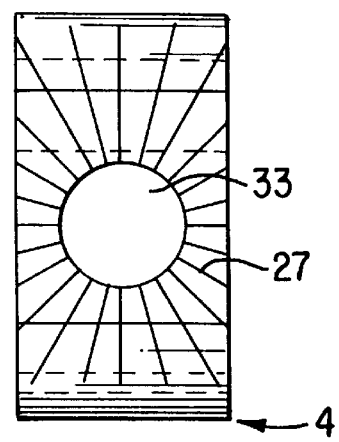

In the embodiment of the invention shown in FIGS. 10 through 12 the connecting slide 105 is of the open type, having a generally rectangular parallelepiped shape and being slit axially by a slot 28 having a circular cross-section first part 29 through which the fastening rod 3 passes and a smaller cross-section second part 30 ending at an enlargement 31. The slot opening 32 enables lateral insertion of the fastening rod 3 when the clamping member is released.

As in the previous embodiment, the slide 105 has a first through-hole 33 and a second through-hole 34 in corresponding relationship and shaped to fit to the screwthreaded cylindrical part 5 of an anchoring element.

The first contact surface 25 has first non-slip projections such as radial ribs 27. The inside surface 22 of the first part 29 of the slot has second non-slip projections such as longitudinal ribs 24, advantageously having a triangular transverse cross-section.

The open slide of FIG. 10 can be fitted to an intermediate part of the fastening rod 3, rather than fitting it at one end thereof and sliding it into position.

Figure 13:
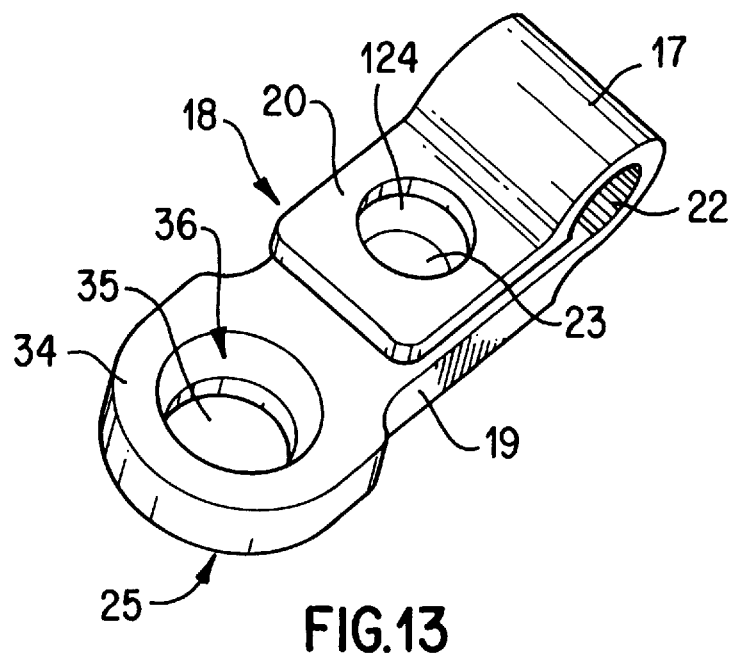
FIGS. 13 and 14 are perspective views of two other embodiments of connecting slides in accordance with the invention.

In the FIG. 13 embodiment of the invention the slide is similar to that of FIGS. 7 through 9 with a clamping part 17, a connecting part 18, a first branch 19 and a second branch 20 each with a respective hole 23 and 124.

However, this embodiment of the invention is different in that the hole 23 in the first branch 19 is screwthreaded to receive the screwthreaded shank of a screw whose head bears on the edges of the smooth through-hole 124 in the second branch 20, the screw clamping the slide and locking it to the fastening rod 3. A second difference is that the first branch 19 has a lateral extension 34 with a hole 35 in it through which an anchoring element shank passes. The hole 35 can advantageously have a hemispherical upper surface 36 to receive the hemispherical head of a conventional bone screw. The lower surface of the hole 35 can itself be flared, for example with a conical shape facing away from the hemispherical upper surface 36, to enable inclination of the shank of the bone screw relative to the axis of the hole 35. The bone screw can then assume various inclinations, independently of the direction of the axes of the hole 35 and of the cylindrical surface 22.

In this case a bone screw can be inserted into a vertebra after inserting it into the hole 35 in the lateral extension 34 after which a screw is screwed into the holes 23 and 124 until the branches 19 and 20 are moved towards each other and clamp the clamping part 17 onto the fastening rod 3.

The cylindrical surface 22 has longitudinal ribs as in the previous embodiments. Likewise the first contact surface 25, or lower surface of the lateral extension 34, which incorporates non-slip projections such as radial ribs. It is to be understood that a slide from FIG. 13 can be used instead of the slides from FIGS. 7 through 12, having the same rotation preventing properties.

Figure 14:
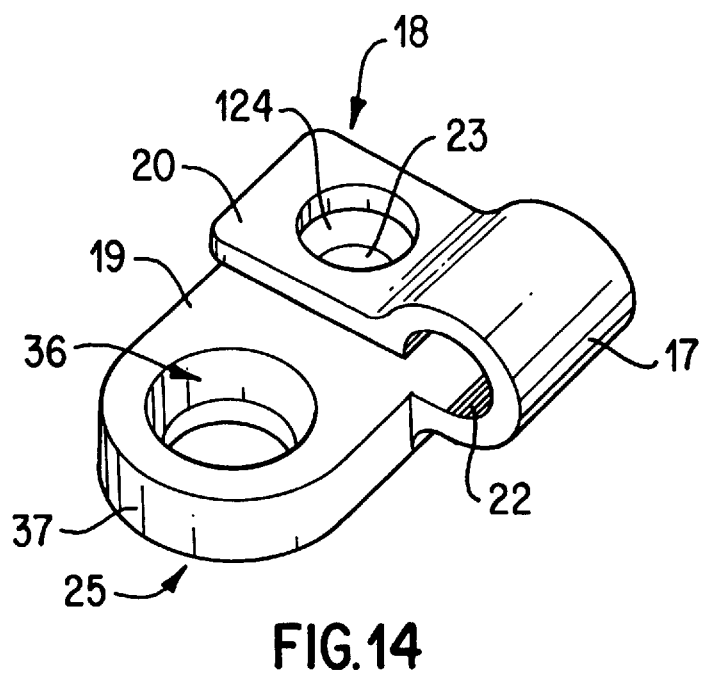

FIG. 14 shows another embodiment of slide, similar to that of FIG. 13, with similar parts identified by the same reference numbers. The difference is that the extension 37 of the first branch 19 extends longitudinally rather than transversely, i.e. in the direction of the longitudinal axis of the cylindrical surface 22.

Figure 15:
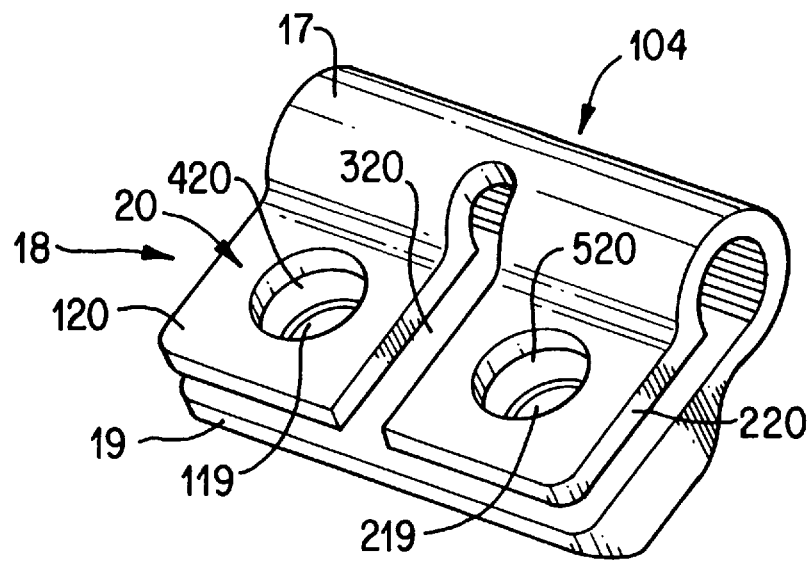
FIG. 15 is a perspective view of a double connecting slide in accordance with the invention.

FIG. 15 shows a double connecting slide 104 in which the first branch 19 of the connecting part 18 is in one piece. The second branch 20 of the connecting part 18 is in two parts 120 and 220 between which is a transverse notch 320. Each part has its respective through-hole 420 and 520 through which pass two clamping screws which are screwed into corresponding screwthreaded holes 119 and 219 in the first branch 19. The FIG. 15 slide 104 is preferably longer than the slide in the previous embodiments, for example twice their length. This version can be used to butt joint two successive fastening rods for treating the spinal column of a patient.

Figure 16:
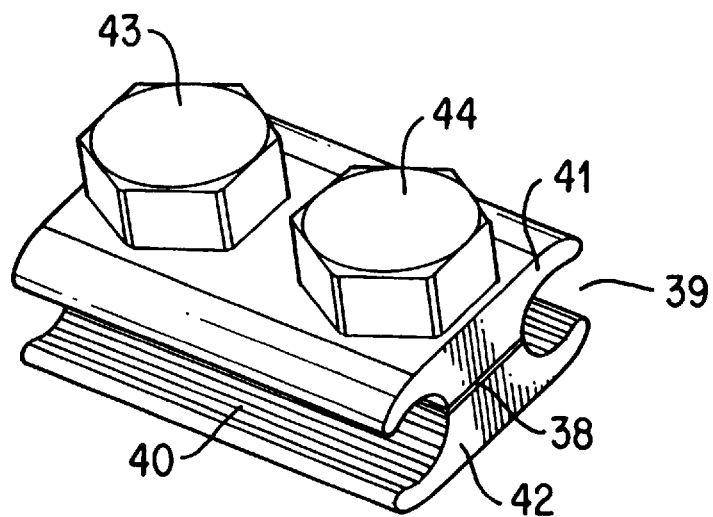
FIG. 16 is a perspective view of another embodiment of double slide.

FIG. 16 shows another embodiment of double slide which has the advantage of being open, incorporating a transverse slot 38 ending in two open cylindrical parts 39 and 40 each receiving one fastening rod. The slide is formed in two parts 41 and 42 clamped together by two screws 43 and 44 to be clamped onto two parallel fastening rods. To prevent rotation of the fastening rods the cylindrical surfaces 39 and 40 have longitudinal ribs, as shown in the figure.

Figure 17:
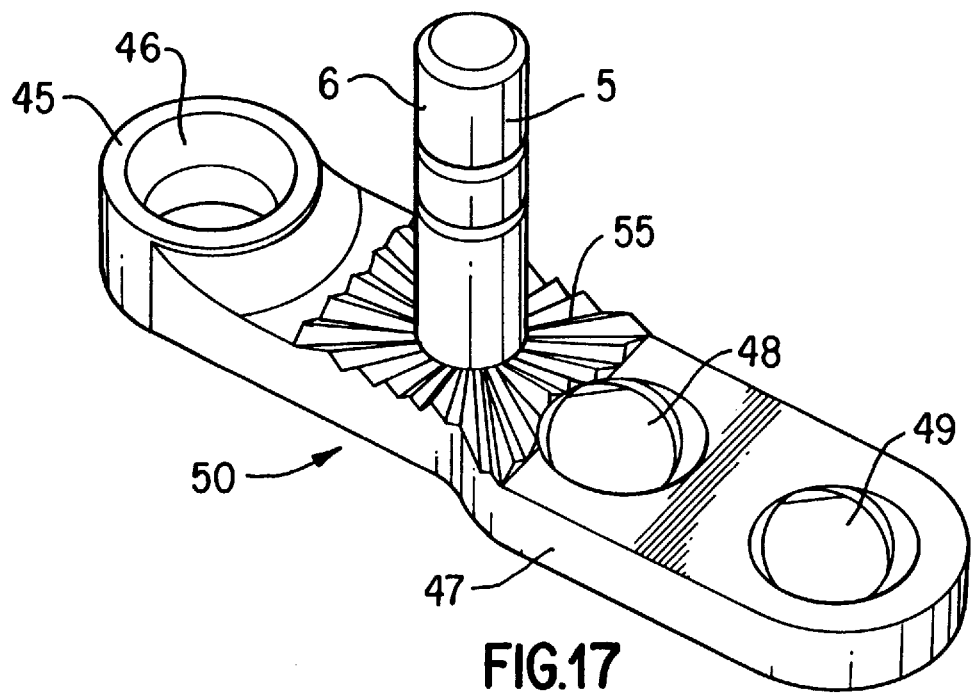
FIG. 17 is a perspective view of a sacral bearing plate that can be used as an anchoring element in implementation of the invention, FIG. 17A showing a similar illio-sacral bearing plate.

FIG. 17 shows another type of anchoring element for implementation of the invention, namely a sacral bearing plate 50. A plate of this kind can be used as an intermediate support between the vertebrae and a slide in the embodiments of FIGS. 7 to 12, 13 or 14.

The sacral bearing plate 50 is in the form of an elongate plate having in its middle portion a screwthreaded cylindrical part 5 with an exterior screwthread 6. One end 45 of the sacral bearing plate is thicker and includes a bore 46 shaped to receive the head of a standard bone screw inserted in the pedicle of the vertebra S1. The other end 47 of the sacral bearing plate includes two further bores 48 and 49 receiving the head of standard bone screws inserted in the sacrum.

The upper surface of the sacral bearing plate 50 includes first non-slip projections such as radial ribs 55 around the base of the screwthreaded cylindrical part 5 and cooperating with the corresponding first non-slip projections on the slides.

The axis of the bore 46 is substantially perpendicular to the plane of the top and the bottom surfaces of the sacral bearing plate 50 and substantially parallel to the axis of the screwthreaded cylindrical part 5. On the other hand, the respective axes of the bores 48 and 49 are oblique, to orient the bone screws that they contain towards the outside and so to facilitate fixing of the sacral bearing plate onto the alae of the sacrum.

Figure 18:
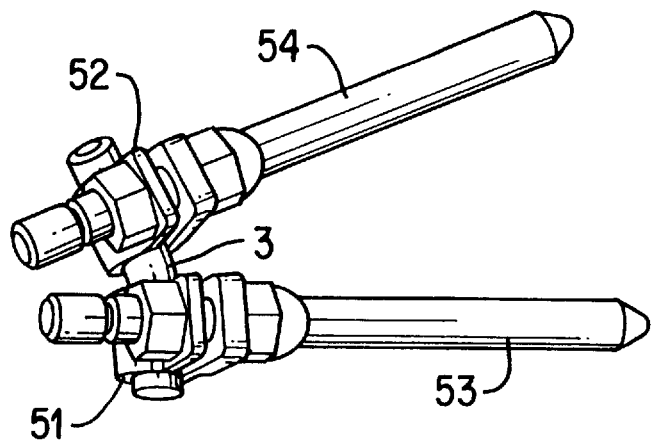
FIGS. 18 and 19 show the benefit of the sacral bearing plate.
Figure 19:
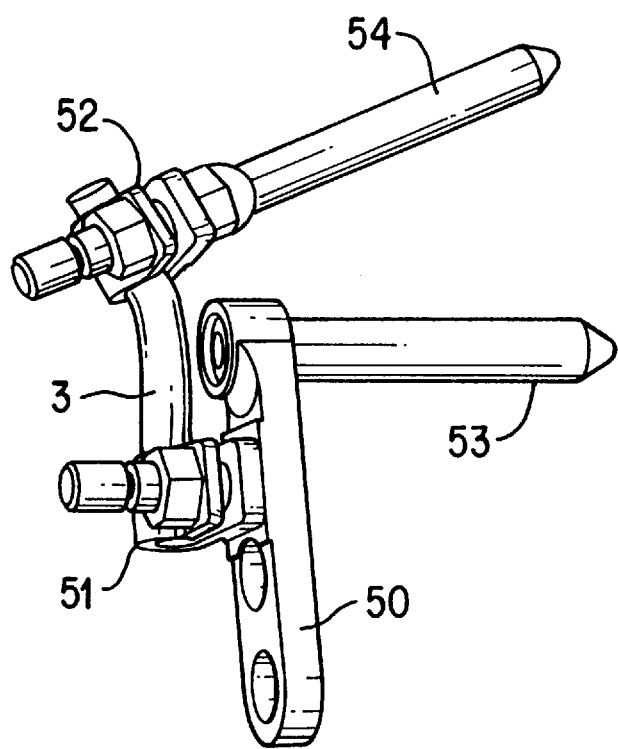

The sacral bearing plate 50 increases the spacing between two successive slides 51 and 52 on the fastening rod 3, the first slide 51 providing the fastening to a first bone screw 53 inserted in S1 via the sacral bearing plate 50 and the second slide 52 providing the connection with a second bone screw 54 inserted in L5. Accordingly, FIG. 18 shows a conventional arrangement in which two bone screws 53 and 54 are joined together only by the slides 51 and 52, which are very close together on the fastening rod 3. Their proximity makes it difficult to position the screws and the slides. Referring to FIG. 19, on the other hand, it can be seen that the interposition of the sacral bearing plate 50 between the bone screw 53 and the slide 51 increases the distance between the slides 51 and 52, considerably facilitating the positioning of the components.

The dimensions of the sacral bearing plate 50 are advantageously chosen so that the distance between the slides 51 and 52 is increased by about 15 mm.

Figure 17A:
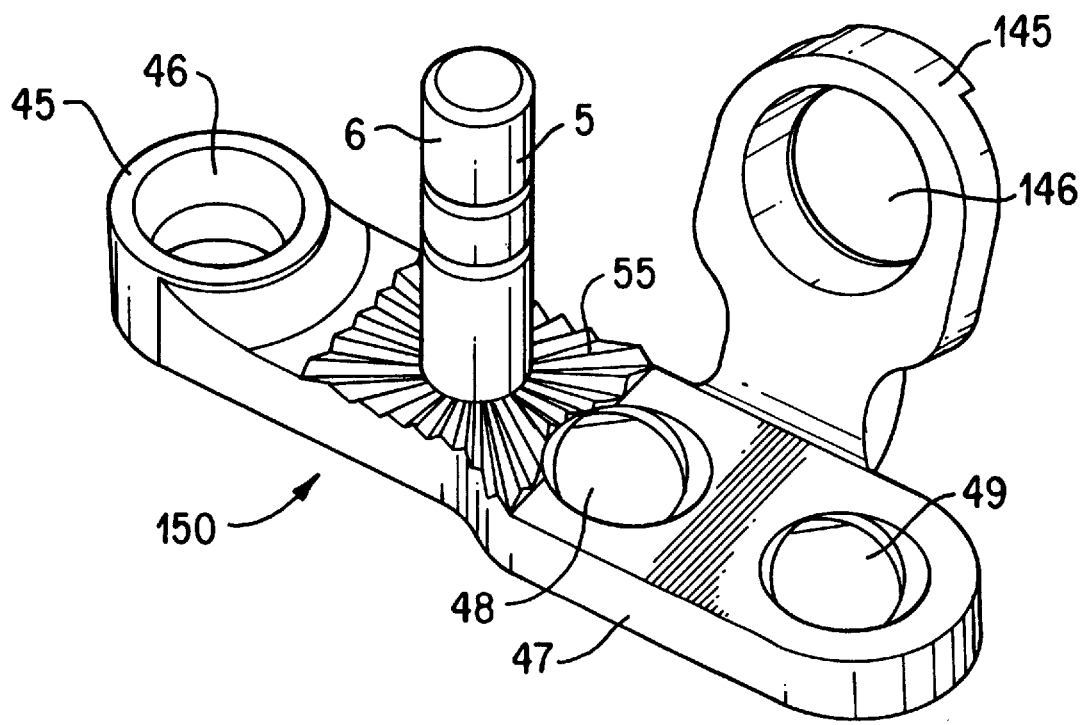

FIG. 17A shows an illio-sacral bearing plate 150 which has the same component parts as the sacral bearing plate 50 from FIG. 17, identified by the same reference numbers, and additionally a lateral anchor lug 145 bent at right angle and having a lateral bore 146 shaped to receive a standard bone screw head.

Figure 20:
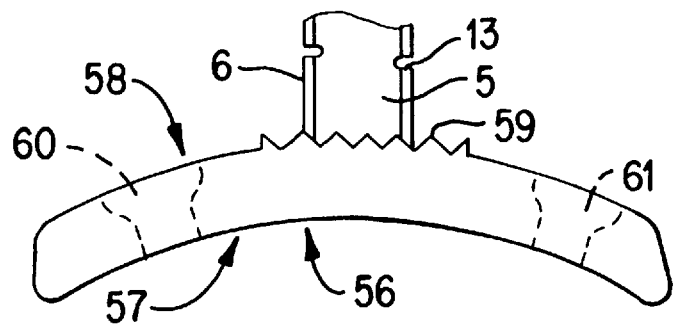
FIGS. 20 and 21 are side and top views of a bearing plate adapted to bear on the body of a vertebra.
Figure 21:
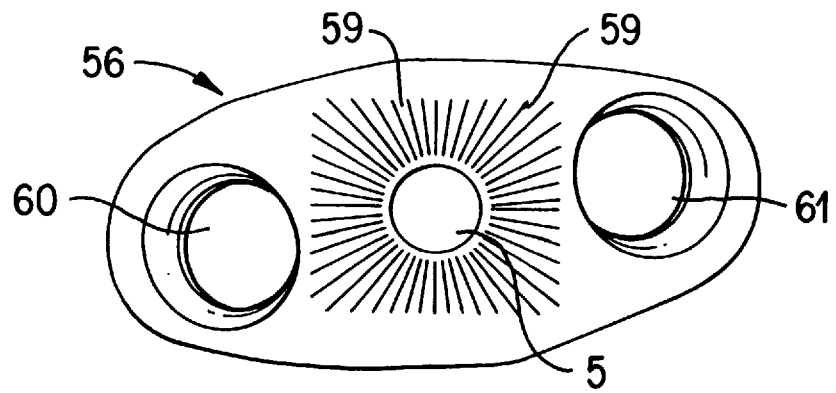

FIGS. 20 and 21 show another type of anchoring element for implementation of the invention in the form of a bearing plate 56 adapted to bear on the body of a vertebra. The bearing plate 56 is a generally oval rigid plate whose opposed bottom and top surfaces 57 and 58 are curved to mate with the shape of the body of the vertebra. The convex top surface 58 includes in its middle part non-slip projections 59 and a cylindrical screwthreaded part 5 for fitting a slide. The top surface 58 with its non-slip projections 59 constitutes a locking plate.

The bearing plate 56 has two bores 60 and 61, one on each side of the cylindrical screwthreaded part 5, and both of generally hemispherical shape to receive the complementary hemispherical shape head of a standard bone screw. Note that the axes of the bores 60 and 61 are offset, as shown in FIG. 21, so that the bone screws enter the vertebra without touching each other, despite the inclination of their respective axes.

Figure 22:
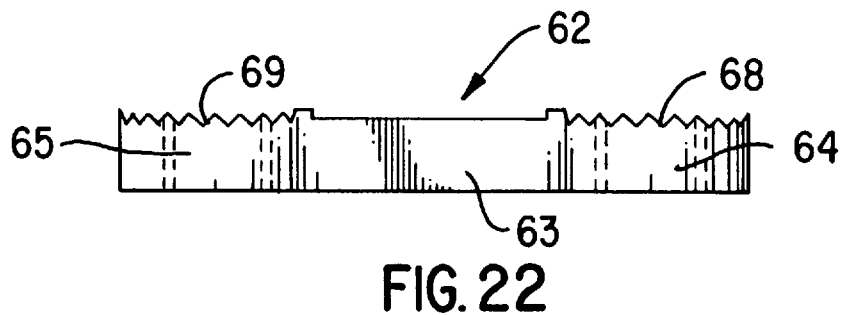
FIGS. 22 and 23 are respectively a side view and a top view of a spacer for linking two parallel fastening rods.
Figure 23:
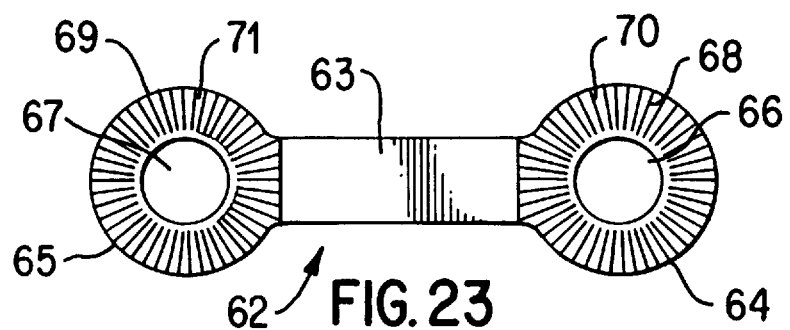

Given that the device of the invention can include two fastening rods 3 situated one on each side of the spinous process of the vertebrae, for better correction and support of the spinal column of the patient, it can be advantageous to fasten the two rods 3 together by means of one or more transverse stabilising systems as shown in FIGS. 22 and 23.

This stabilising system includes a spacer 62 having a central part 63 ending in two wider end parts 64 and 65 each having a respective through-hole 66 and 67 and a bearing surface 68 and 69 having first non-slip projections such as radial ribs 70 and 71. The holes 66 and 67 are preferably screwthreaded. The spacer 62 is connected to the fastening rods 3 by connecting slides whose first contact surfaces 25 bear on the ribbed bearing surfaces 68 and 69 of the spacer, preventing any rotation. Screws clamp each slide onto the corresponding surface 68 or 69 of the spacer 62. In this way the distance between the two fastening rods 3 can be adjusted by offsetting the slides relative to each other in the longitudinal direction, so that the spacer 62 assumes an oblique position.

The device of the invention enables the use of a rod or of a plurality of rod elements whose curvature is suited to the part of the spinal column to be treated.

The slides 4 are easy to fit to the fastening rod 3 because they are threaded over each end of the latter, or engaged from the side, and slide freely on the rod 3 regardless of its curvature.

The deformation of the spinal column is to be reduced in three dimensions. It is necessary to transform a scoliotic curvature oriented in a plane close to the frontal plane into a physiological curvature in the sagittal plane and having a normal lumbar lordotic, thoracic and kyphotic curvature.

The fastening rod is first given a shape close to the normal physiological curvature and positioned in the saggital plane of the patient, its two ends being fixed by means of anchoring elements and correctly clamped slides. The non-slip projections of the invention provide very effective immobilisation of the rod, both in translation and, more importantly, in rotation. Anchoring elements are inserted in or on other intermediate vertebrae. The anchorages nearest the rod are engaged in the slides and locked to immobilise the rod in the saggital plane and also to prevent it rotating. The most distant anchorages in the concave part of the curvature can be engaged because of the length of the screwthreaded cylindrical part 5 of the anchoring elements. Once the end of the screwthreaded cylindrical part has been inserted into the bore of the connecting slide 4 fitted to the rod but not yet clamped onto the rod, progressive tightening of the nut 8 moves the anchorage point towards the fastening rod, progressively reducing the vertebral curvature. When the spinal column has no further elasticity, the fastening rod 3 is deformed and provides correction in an intermediate position of maximal reduction.

The device of the invention enables the screwthreaded cylindrical part of each intermediate anchoring element already fitted to be inserted into the bore of a slide and fixed rigidly to the rod, in alignment with anchoring elements above and below it, to achieve the required straightening of the vertebrae by screwing and tightening of the nuts to lock the slides onto the rod.

The device of the invention can be fitted either in front of or behind the spinal column of a patient.

Because of the non-slip projections the device of the invention can be fitted in a much shorter time than prior art devices, given the increased facility with which the surgeon can tighten or loosen the slide clamping nuts 8 without modifying the penetration of the bone screws into the bone.

It is to be understood that a device of the invention can include screw, hook or plate type anchoring elements, depending on the treatment required, or a combination of any two or three of these types of anchoring element which are independent of each other.

Figure 24:
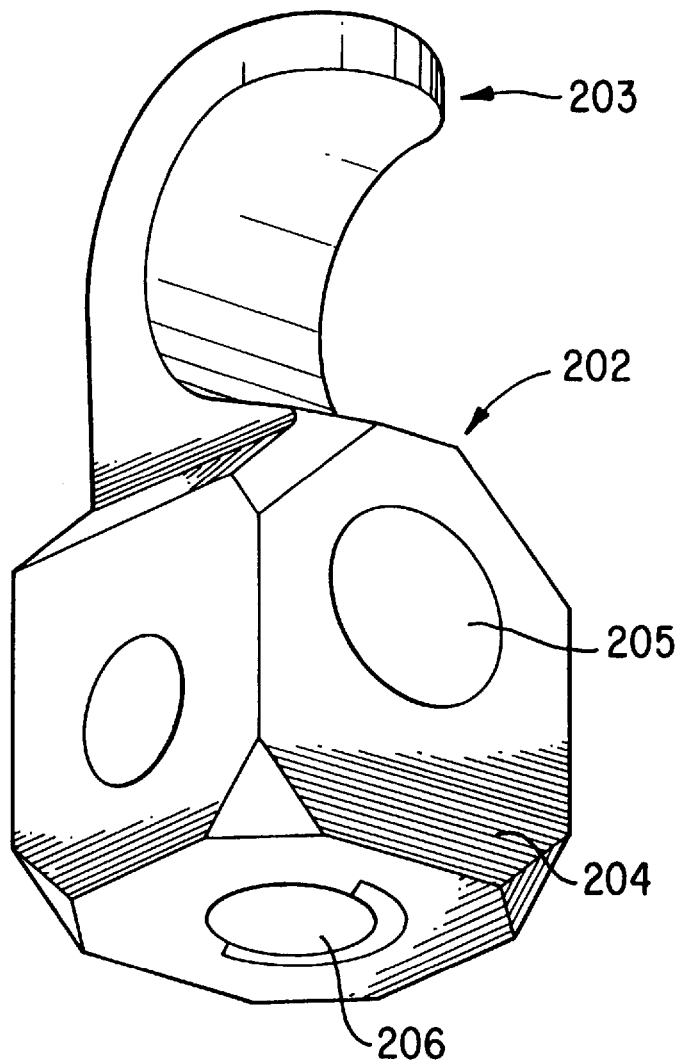
FIG. 24 is a perspective view of an end lamina hook.

Furthermore, the specific components of the invention enable assembly of two opposed hooks associated with respective slides mounted on one and the same fastening rod 3, to form a pedicle-lamina clamp. This is shown by the hooks 200 and 202 in the upper part of the device shown in FIGS. 1 to 3. The pedicle hook 200 is shaped like the hook 2 shown in FIG. 5. The hook 202 is an end lamina hook as shown in FIG. 24, in which the hook-shape curved part 203 is attached to a generally cubical body 204 through which is a transverse bore 205 for the fastening rod 3. A screw inserted into an axial screwthreaded hole 206 bears on the rod passing through the transverse bore 205 and locks the hook 202 to the rod. The hook part 203 is near the axis of the fastening rod 3. The two opposed hooks 200 and 202 can be fitted so that one is in bearing engagement with the pedicle and the other is in bearing engagement with the lamina of the same vertebra, conforming to the natural offset between the lamina and the pedicle. Because of the rotational locking of the pedicle hooks, procured by the non-slip projections, particularly effective attachment is achieved to certain upper vertebrae, without using screw type anchoring elements.

It is to be understood that a pedicle-lamina clamp of this kind can be used independently of the presence or the nature of other anchoring elements, and that it has its own functions and advantages.

The present invention is not limited to the embodiments explicitly described but encompasses various variants and generalisations thereof within the scope of the following claims.

We claim:

1. Spinal therapy device comprising:
    vertebral anchoring elements (1, 2, 200, 202, 50, 56) having a longitudinal axis and having an anchoring part (9, 15, 50, 150, 56) extending along the longitudinal axis and shaped to be anchored to the bone of a vertebra and extended by a male screwthreaded cylindrical part (5) onto which a clamping nut (8) is screwed, the male screwthreaded cylindrical part extending alone the longitudinal axis and having a base,
    at least one circular cross-section fastening rod (3) having a smooth outside surface,
    connecting slides (4) for connecting anchoring elements (1, 2, 200, 202, 50, 56) to the fastening rod (3), the connecting slides (4) having a clamping part (17) and a connecting part (18), the clamping part (17) having inside surfaces (22) shaped to surround a section of the fastening rod (3) and being deformable for selectively clamping said clamping part to and releasing said clamping part from the fastening rod (3), the connecting part (18) having a first branch (19) and a second branch (20) extending laterally and parallel to each other from two lips of a longitudinal slot (100) in the clamping part (17), said branches (19, 20) of the connecting part having corresponding through-holes (23, 124) for receiving the male screwthreaded cylindrical part (5) of one of said anchoring elements for clamping the branches (19, 20) together and thereby clamping the clamping part (17),
    wherein:
        the anchoring elements (1, 2, 200, 202, 50, 56) include a locking plate (7) with a bearing surface (12) generally perpendicular to the axis of the male screwthreaded cylindrical part (5) and extending from the base of the male screwthreaded cylindrical part,
        the bearing surface (12) of the locking plate (7) includes first non-slip projections (16),
        the first branch (19) of the connecting part (18) of a corresponding connecting slide (4), having a first contact surface (25) adapted to bear against the bearing surface (12) of one of said anchoring elements, includes corresponding first non-slip projections (27) to oppose any lateral displacement and any rotation of the connecting slide (4) around the male screwthreaded cylindrical part of said one of said anchoring elements after clamping of the nut (8) against the opposite second contact surface (26) of the second branch (20) of the connecting part (18),
        wherein the non-slip projections (16, 27) comprise means for preventing rotation of the anchoring element while the nut is being tightened, and for enabling adjustment of an angular position of the connecting slides on the anchoring elements before the nut has been completely tightened.

2. Device according to claim 1 wherein the first non-slip projections (16, 27) comprise radial ribs respectively disposed on the bearing surface (12) from the base of the screwthreaded cylindrical part (5) and on the first contact surface (25) from the edge of the corresponding throughhole (23).

3. Device according to claim 1 wherein the device includes as anchoring element(s) one or more doublethreaded bone screws (1), the screwthreaded cylindrical part (5) of an anchoring element constituting a first screwthreaded part, the bone screws (1) including a coaxial second cylindrical screwthreaded part (9) on the opposite side of the locking plate (7), the second screwthreaded part (9) being adapted to be screwed into bone.

4. Device according to claim 1 wherein the device includes as anchoring element(s) one or more hooks (2) in which the hook body (15) constitutes the anchoring part and in which the rear wall of the hook, perpendicular to the axis of the screwthreaded cylindrical part (5), provides a locking plate and carries the first non-slip projections (16).

5. Spinal therapy device comprising:
    vertebral anchoring elements (1, 2, 200, 202, 50, 56) having an anchoring part (9, 15, 50, 150, 56) shaped to be anchored to the bone of a vertebra and extended by a screwthreaded cylindrical part (5) onto which a clamping nut (8) is screwed, the screwthreaded cylindrical part having a base,
    at least one circular cross-section fastening rod (3) having a smooth outside surface,
    connecting slides (4) for connecting anchoring elements (1, 2, 200, 202, 50, 56) to the fastening rod (3), the connecting slides (4) having a clamping part (17) and a connecting part (18), the clamping part (17) having inside surfaces (22) shaped to surround a section of the fastening rod (3) and being deformable for selectively clamping said clamping part to and releasing said clamping part from the fastening rod (3), the connecting part (18) having a first branch (19) and a second branch (20) extending laterally and parallel to each other from two lips of a longitudinal slot (100) in the clamping part (17), said branches (19, 20) of the connecting part having corresponding through-holes (23, 124) for receiving the screwthreaded cylindrical part (5) of one of said anchoring elements for clamping the branches (19, 20) together and thereby clamping the clamping part (17), wherein:
  the anchoring elements (1, 2, 200, 202, 50, 56) include a locking plate (7) with a bearing surface (12) generally perpendicular to the axis of the screwthreaded cylindrical part (5) and extending from the base of the screwthreaded cylindrical part,
  the bearing surface (12) of the locking plate (7) includes first non-slip projections (16),
  the first branch (19) of the connecting part (18) of a corresponding connecting slide (4), having a first contact surface (25) adapted to bear against the bearing surface (12) of one of said anchoring elements, includes corresponding first non-slip projections (27) to oppose any rotation and any lateral displacement of the connecting slide (4) relative to said one of said anchoring elements after clamping of the nut (8) against the opposite second contact surface (26) of the second branch (20) of the connecting part (18), and
  the device includes as anchoring element(s) at least one component selected from the group consisting of a sacral bearing plate (50) and an illio-sacral bearing plate (150), said component being of generally elongate shape, having in its middle part the screwthreaded cylindrical part (5) flanked by the bearing surface with first non-slip projections (55), having in the vicinity of a first end (45) a thicker part through which is a bore (46) for a standard bone screw, and having near its second end (47) two other bores (48, 49) for standard bone screws with the axis inclined.

6. Spinal therapy device comprising:
vertebral anchoring elements (1, 2, 200, 202, 50, 56) having an anchoring part (9, 15, 50, 150, 56) shaped to be anchored to the bone of a vertebra and extended by a screwthreaded cylindrical part (5) onto which a clamping nut (8) is screwed, the screwthreaded cylindrical part having a base,
at least one circular cross-section fastening rod (3) having a smooth outside surface,
connecting slides (4) for connecting anchoring elements (1, 2, 200, 202, 50, 56) to the fastening rod (3), the connecting slides (4) having a clamping part (17) and a connecting part (18), the clamping part (17) having inside surfaces (22) shaped to surround a section of the fastening rod (3) and being deformable for selectively clamping said clamping part to and releasing said clamping part from the fastening rod (3), the connecting part (18) having a first branch (19) and a second branch (20) extending laterally and parallel to each other from two lips of a longitudinal slot (100) in the clamping part (17), said branches (19, 20) of the connecting part having corresponding through-holes (23, 124) for receiving the screwthreaded cylindrical part (5) of one of said anchoring elements for clamping the branches (19, 20) together and thereby clamping the clamping part (17),
wherein:
  the anchoring elements (1, 2, 200, 202, 50, 56) include a locking plate (7) with a bearing surface (12) generally perpendicular to the axis of the screwthreaded cylindrical part (5) and extending from the base of the screwthreaded cylindrical part,
  the bearing surface (12) of the locking plate (7) includes first non-slip projections (16),
  the first branch (19) of the connecting part (18) of a corresponding connecting slide (4), having a first contact surface (25) adapted to bear against the bearing surface (12) of one of said anchoring elements, includes corresponding first non-slip projections (27) to oppose any rotation and any lateral displacement of the connecting slide (4) relative to said one of said anchoring elements after clamping of the nut (8) against the opposite second contact surface (26) of the second branch (20) of the connecting part (18), and
  wherein the device comprises as clamping member(s) a bearing plate (56) adapted to bear on the body of a vertebra, having a curved oval shape with the screwthreaded cylindrical part (5) on the middle part of its convex side (58) with non-slip projections (59) and, on either side of said middle part, two bores (60, 61) for bone screws with offset axes.

7. Spinal therapy device comprising:
vertebral anchoring elements (1, 2, 200, 202, 50, 56) having an anchoring part (9, 15, 50, 150, 56) shaped to be anchored to the bone of a vertebra and extended by a screwthreaded cylindrical part (5) onto which a clamping nut (8) is screwed, the screwthreaded cylindrical part having a base,
at least one circular cross-section fastening rod (3) having a smooth outside surface,
connecting slides (4) for connecting anchoring elements (1, 2, 200, 202, 50, 56) to the fastening rod (3), the connecting slides (4) having a clamping part (17) and a connecting part (18), the clamping part (17) having inside surfaces (22) shaped to surround a section of the fastening rod (3) and being deformable for selectively clamping said clamping part to and releasing said clamping part from the fastening rod (3), the connecting part (18) having a first branch (19) and a second branch (20) extending laterally and parallel to each other from two lips of a longitudinal slot (100) in the clamping part (17), said branches (19, 20) of the connecting part having corresponding through-holes (23, 124) for receiving the screwthreaded cylindrical part (5) of one of said anchoring elements for clamping the branches (19, 20) together and thereby clamping the clamping part (17),
wherein:
  the anchoring elements (1, 2, 200, 202, 50, 56) include a locking plate (7) with a bearing surface (12) generally perpendicular to the axis of the screwthreaded cylindrical part (5) and extending from the base of the screwthreaded cylindrical part,
  the bearing surface (12) of the locking plate (7) includes first non-slip projections (16),
  the first branch (19) of the connecting part (18) of a corresponding connecting slide (4), having a first contact surface (25) adapted to bear against the bearing surface (12) of one of said anchoring elements, includes corresponding first non-slip projections (27) to oppose any rotation and any lateral displacement of the connecting slide (4) relative to said one of said anchoring elements after clamping of the nut (8) against the opposite second contact surface (26) of the second branch (20) of the connecting part (18), and
  wherein the connecting slide (105) is of generally parallelepiped shape, slit axially by a slot (28) having a circular cross-section first part (29) for the fastening rod (3) to pass through and a smaller cross-section second part (30) ending at an enlargement (31), the first part (29) communicating with a slot opening (32), the slot opening (32) enabling lateral insertion of the fastening rod (3) when the clamping member is released.

8. Spinal therapy device comprising:

vertebral anchoring elements (1, 2, 200, 202, 50, 56) having a longitudinal axis and having an anchoring part (9, 15, 50, 150, 56) extending along the longitudinal axis and shaped to be anchored to the bone of a vertebra and extended by a screwthreaded cylindrical part (5) onto which a clamping nut (8) is screwed, the screwthreaded cylindrical part extending along the longitudinal axis and having a base, at least one circular cross-section fastening rod (3) having a smooth outside surface, connecting slides (4) for connecting anchoring elements (1, 2, 200, 202, 50, 56) to the fastening rod (3), the connecting slides (4) having a clamping part (17) and a connecting part (18), the clamping part (17) having inside surfaces (22) shaped to surround a section of the fastening rod (3) and being deformable for selectively clamping said clamping part to and releasing said clamping part from the fastening rod (3), the connecting part (18) having a first branch (19) and a second branch (20) extending laterally and parallel to each other from two lips of a longitudinal slot (100) in the clamping part (17), said branches (19, 20) of the connecting part having corresponding through-holes (23, 124) for receiving the screwthreaded cylindrical part (5) of one of said anchoring elements for clamping the branches (19, 20) together and thereby clamping the clamping part (17), wherein:
the anchoring elements (1, 2, 200, 202, 50, 56) include a locking plate (7) with a bearing surface (12) generally perpendicular to the axis of the screwthreaded cylindrical part (5) and extending from the base of the screwthreaded cylindrical part,
the bearing surface (12) of the locking plate (7) includes first non-slip projections (16),
the first branch (19) of the connecting part (18) of a corresponding connecting slide (4), having a first contact surface (25) adapted to bear against the bearing surface (12) of one of said anchoring elements, includes corresponding first non-slip projections (27) to oppose any rotation and any lateral displacement of the connecting slide (4) relative to said one of said anchoring elements after clamping of the nut (8) against the opposite second contact surface (26) of the second branch (20) of the connecting part (18),
wherein the device includes an assembly of two opposed hooks (200, 202) associated with respective slides (4) mounted on a common fastening rod (3), one adapted for bearing engagement on the lamina and the other for bearing engagement on the pedicle of the same vertebra, one hook (200) being laterally offset relative to another hook (202) by its respective slide (4).

9. A spinal therapy device comprising:

a plurality of vertebral anchoring elements having a longitudinal axis and shaped to be anchored into bone of a vertebra, the anchoring elements including male screwthreaded cylindrical parts which extend along the longitudinal axis and are connected respectively to a plurality of clamping nuts, at least one fastening rod having a circular cross-section and having a smooth outside surface, and a plurality of connecting slides for connecting the anchoring elements to the fastening rod, wherein the anchoring elements each have locking plates, the locking plates having bearing surfaces, the bearing surfaces having a plurality of non-slip projections, and wherein the connecting slides also include a plurality of non-slip projections, wherein the non-slip projections of the connecting slides comprise means for opposing any lateral displacement and any rotation of the connecting slides around the male screwthreaded cylindrical parts of the anchoring elements after clamping of one of the nuts, the non-slip projections (16, 27) also comprising means for preventing rotation of the anchoring element while the nut is being tightened, and for enabling adjustment of an angular position of the connecting slides on the anchoring elements before the nut has been completely tightened.

10. Spinal therapy device comprising:

vertebral anchoring elements (1, 2, 200, 202, 50, 56) having an anchoring part (9, 15, 50, 150, 56) shaped to be anchored to the bone of a vertebra and extended by a screwthreaded cylindrical part (5) onto which a clamping nut (8) is screwed, the screwthreaded cylindrical part having a base, at least one circular cross-section fastening rod (3) having a smooth outside surface, connecting slides (4) for connecting anchoring elements (1, 2, 200, 202, 50, 56) to the fastening rod (3), the connecting slides (4) having a clamping part (17) and a connecting part (18), the clamping part (17) having inside surfaces (22) shaped to surround a section of the fastening rod (3) and being deformable for selectively clamping said clamping part to and releasing said clamping part from the fastening rod (3), the connecting part (18) having a first branch (19) and a second branch (20) extending laterally and parallel to each other from two lips of a longitudinal slot (100) in the clamping part (17), said branches (19, 20) of the connecting part having corresponding through-holes (23, 124) for receiving the screwthreaded cylindrical part (5) of one of said anchoring elements for clamping the branches (19, 20) together and thereby clamping the clamping part (17), wherein:
the anchoring elements (1, 2, 200, 202, 50, 56) include a locking plate (7) with a bearing surface (12) generally perpendicular to the axis of the screwthreaded cylindrical part (5) and extending from the base of the screwthreaded cylindrical part,
the bearing surface (12) of the locking plate (7) includes first non-slip projections (16),
the first branch (19) of the connecting part (18) of a corresponding connecting slide (4), having a first contact surface (25) adapted to bear against the bearing surface (12) of one of said anchoring elements, includes corresponding first non-slip projections (27) to oppose any rotation and any lateral displacement of the connecting slide (4) relative to said one of said anchoring elements after clamping of the nut (8) against the opposite second contact surface (26) of the second branch (20) of the connecting part (18),
wherein the device includes as anchoring element(s) at least one component selected from the group consisting of a sacral bearing plate (50) and an illio-sacral bearing plate (150), said component being of generally elongate shape, having in its middle part the screwthreaded cylindrical part (5) flanked by the bearing surface with first non-slip projections (55), having in the vicinity of a first end (45) a thicker part through which is a bore (46) for a standard bone screw, and having near its second end (47) two other bores (48, 49) for standard bone screws with the axis inclined.

11. Spinal therapy device comprising:

vertebral anchoring elements (1, 2, 200, 202, 50, 56) having an anchoring part (9, 15, 50, 150, 56) shaped to be anchored to the bone of a vertebra and extended by a screwthreaded cylindrical part (5) onto which a clamping nut (8) is screwed, the screwthreaded cylindrical part having a base, at least one circular cross-section fastening rod (3) having a smooth outside surface, connecting slides (4) for connecting anchoring elements (1, 2, 200, 202, 50, 56) to the fastening rod (3), the connecting slides (4) having a clamping part (17) and a connecting part (18), the clamping part (17) having inside surfaces (22) shaped to surround a section of the fastening rod (3) and being deformable for selectively clamping said clamping part to and releasing said clamping part from the fastening rod (3), the connecting part (18) having a first branch (19) and a second branch (20) extending laterally and parallel to each other from two lips of a longitudinal slot (100) in the clamping part (17), said branches (19, 20) of the connecting part having corresponding through-holes (23, 124) for receiving the screwthreaded cylindrical part (5) of one of said anchoring elements for clamping the branches (19, 20) together and thereby clamping the clamping part (17), wherein:

the anchoring elements (1, 2, 200, 202, 50, 56) include a locking plate (7) with a bearing surface (12) generally perpendicular to the axis of the screwthreaded cylindrical part (5) and extending from the base of the screwthreaded cylindrical part, the bearing surface (12) of the locking plate (7) includes first non-slip projections (16), the first branch (19) of the connecting part (18) of a corresponding connecting slide (4), having a first contact surface (25) adapted to bear against the bearing surface (12) of one of said anchoring elements, includes corresponding first non-slip projections (27) to oppose any rotation and any lateral displacement of the connecting slide (4) relative to said one of said anchoring elements after clamping of the nut (8) against the opposite second contact surface (26) of the second branch (20) of the connecting part (18), wherein the device comprises as clamping member(s) a bearing plate (56) adapted to bear on the body of a vertebra, having a curved oval shape with the screwthreaded cylindrical part (5) on the middle part of its convex side (58) with non-slip projections (59) and, on either side of said middle part, two bores (60, 61) for bone screws with offset axes.

12. Spinal therapy device comprising:

vertebral anchoring elements (1, 2, 200, 202, 50, 56) having an anchoring part (9, 15, 50, 150, 56) shaped to be anchored to the bone of a vertebra and extended by a screwthreaded cylindrical part (5) onto which a clamping nut (8) is screwed, the screwthreaded cylindrical part having a base, at least one circular cross-section fastening rod (3) having a smooth outside surface, connecting slides (4) for connecting anchoring elements (1, 2, 200, 202, 50, 56) to the fastening rod (3), the connecting slides (4) having a clamping part (17) and a connecting part (18), the clamping part (17) having inside surfaces (22) shaped to surround a section of the fastening rod (3) and being deformable for selectively clamping said clamping part to and releasing said clamping part from the fastening rod (3), the connecting part (18) having a first branch (19) and a second branch (20) extending laterally and parallel to each other from two lips of a longitudinal slot (100) in the clamping part (17), said branches (19, 20) of the connecting part having corresponding through-holes (23, 124) for receiving the screwthreaded cylindrical part (5) of one of said anchoring elements for clamping the branches (19, 20) together and thereby clamping the clamping part (17), wherein:

the anchoring elements (1, 2, 200, 202, 50, 56) include a locking plate (7) with a bearing surface (12) generally perpendicular to the axis of the screwthreaded cylindrical part (5) and extending from the base of the screwthreaded cylindrical part, the bearing surface (12) of the locking plate (7) includes first non-slip projections (16), the first branch (19) of the connecting part (18) of a corresponding connecting slide (4), having a first contact surface (25) adapted to bear against the bearing surface (12) of one of said anchoring elements, includes corresponding first non-slip projections (27) to oppose any rotation and any lateral displacement of the connecting slide (4) relative to said one of said anchoring elements after clamping of the nut (8) against the opposite second contact surface (26) of the second branch (20) of the connecting part (18), wherein the device includes a double connecting slide (104) in which at least one branch (20) of the branches (19, 20) of the connecting part (18) has two parts (120, 220) separated by a transverse notch (320) and each having holes (420, 520) for clamping screws corresponding to screw-threaded holes (119, 219) on the other branch (19).

13. Spinal therapy device comprising:

vertebral anchoring elements (1, 2, 200, 202, 50, 56) having an anchoring part (9, 15, 50, 150, 56) shaped to be anchored to the bone of a vertebra and extended by a screwthreaded cylindrical part (5) onto which a clamping nut (8) is screwed, the screwthreaded cylindrical part having a base, at least one circular cross-section fastening rod (3) having a smooth outside surface, connecting slides (4) for connecting anchoring elements (1, 2, 200, 202, 50, 56) to the fastening rod (3), the connecting slides (4) having a clamping part (17) and a connecting part (18), the clamping part (17) having inside surfaces (22) shaped to surround a section of the fastening rod (3) and being deformable for selectively clamping said clamping part to and releasing said clamping part from the fastening rod (3), the connecting part (18) having a first branch (19) and a second branch (20) extending laterally and parallel to each other from two lips of a longitudinal slot (100) in the clamping part (17), said branches (19, 20) of the connecting part having corresponding through-holes (23, 124) for receiving the screwthreaded cylindrical part (5) of one of said anchoring elements for clamping the branches (19, 20) together and thereby clamping the clamping part (17), wherein:
the anchoring elements (1, 2, 200, 202, 50, 56) include a locking plate (7) with a bearing surface (12) generally perpendicular to the axis of the screwthreaded cylindrical part (5) and extending from the base of the screwthreaded cylindrical part, the bearing surface (12) of the locking plate (7) includes first non-slip projections (16), the first branch (19) of the connecting part (18) of a corresponding connecting slide (4), having a first contact surface (25) adapted to bear against the bearing surface (12) of one of said anchoring elements, includes corresponding first non-slip projections (27) to oppose any rotation and any lateral displacement of the connecting slide (4) relative to said one of said anchoring elements after clamping of the nut (8) against the opposite second contact surface (26) of the second branch (20) of the connecting part (18), wherein the first branch (19), including the first contact surface (25) adapted to bear against the bearing surface (12) of said one of the anchoring elements, is offset outwardly relative to an axis (II—II) of the clamping part (17), and wherein the first connecting branch (19), including the first contact surface (25), includes a lateral extension (34) spaced apart from the second connecting branch (20) and having a hole (35) for a pedicle screw to pass through, the second connecting branch (20) includes a smooth through-hole (124) for receiving the head of a clamping screw whose shank is screwed into a corresponding screwthreaded hole (23) on the first connecting branch (19).

14. Spinal therapy device comprising:

vertebral anchoring elements (1, 2, 200, 202, 50, 56) having an anchoring part (9, 15, 50, 150, 56) shaped to be anchored to the bone of a vertebra and extended by a screwthreaded cylindrical part (5) onto which a clamping nut (8) is screwed, the screwthreaded cylindrical part having a base, at least one circular cross-section fastening rod (3) having a smooth outside surface, connecting slides (4) for connecting anchoring elements (1, 2, 200, 202, 50, 56) to the fastening rod (3), the connecting slides (4) having a clamping part (17) and a connecting part (18), the clamping part (17) having inside surfaces (22) shaped to surround a section of the fastening rod (3) and being deformable for selectively clamping said clamping part to and releasing said clamping part from the fastening rod (3), the connecting part (18) having a first branch (19) and a second branch (20) extending laterally and parallel to each other from two lips of a longitudinal slot (100) in the clamping part (17), said branches (19, 20) of the connecting part having corresponding through-holes (23, 124) for receiving the screwthreaded cylindrical part (5) of one of said anchoring elements for clamping the branches (19, 20) together and thereby clamping the clamping part (17), wherein:
the anchoring elements (1, 2, 200, 202, 50, 56) include a locking plate (7) with a bearing surface (12) generally perpendicular to the axis of the screwthreaded cylindrical part (5) and extending from the base of the screwthreaded cylindrical part, the bearing surface (12) of the locking plate (7) includes first non-slip projections (16), the first branch (19) of the connecting part (18) of a corresponding connecting slide (4), having a first contact surface (25) adapted to bear against the bearing surface (12) of one of said anchoring elements, includes corresponding first non-slip projections (27) to oppose any rotation and any lateral displacement of the connecting slide (4) relative to said one of said anchoring elements after clamping of the nut (8) against the opposite second contact surface (26) of the second branch (20) of the connecting part (18), wherein the device includes:
two fastening rods (3) with their respective anchoring elements (1) and slides (4), at least one spacer (62) connected to each fastening rod (3) by respective slides (4) on which it bears through surfaces (68, 69) with first non-slip projections (70, 71).

15. Spinal therapy device comprising:

vertebral anchoring elements (1, 2, 200, 202, 50, 56) having an anchoring part (9, 15, 50, 150, 56) shaped to be anchored to the bone of a vertebra and extended by a screwthreaded cylindrical part (5) onto which a clamping nut (8) is screwed, the screwthreaded cylindrical part having a base, at least one circular cross-section fastening rod (3) having a smooth outside surface, connecting slides (4) for connecting anchoring elements (1, 2, 200, 202, 50, 56) to the fastening rod (3), the connecting slides (4) having a clamping part (17) and a connecting part (18), the clamping part (17) having inside surfaces (22) shaped to surround a section of the fastening rod (3) and being deformable for selectively clamping said clamping part to and releasing said clamping part from the fastening rod (3), the connecting part (18) having a first branch (19) and a second branch (20) extending laterally and parallel to each other from two lips of a longitudinal slot (100) in the clamping part (17), said branches (19, 20) of the connecting part having corresponding through-holes (23, 124) for receiving the screwthreaded cylindrical part (5) of one of said anchoring elements for clamping the branches (19, 20) together and thereby clamping the clamping part (17), wherein:
the anchoring elements (1, 2, 200, 202, 50, 56) include a locking plate (7) with a bearing surface (12) generally perpendicular to the axis of the screwthreaded cylindrical part (5) and extending from the base of the screwthreaded cylindrical part, the bearing surface (12) of the locking plate (7) includes first non-slip projections (16), the first branch (19) of the connecting part (18) of a corresponding connecting slide (4), having a first contact surface (25) adapted to bear against the bearing surface (12) of one of said anchoring elements, includes corresponding first non-slip projections (27) to oppose any rotation and any lateral displacement of the connecting slide (4) relative to said one of said anchoring elements after clamping of the nut (8) against the opposite second contact surface (26) of the second branch (20) of the connecting part (18), wherein the first branch (19), including the first contact surface (25) adapted to bear against the bearing surface (12) of said one of the anchoring elements, is offset outwardly relative to an axis (II—II) of the clamping part (17), and wherein:

the first connecting branch (19), including the first contact surface (25), includes an axial extension (37) spaced apart from the second connecting branch (20) and having a hole (35) for a pedicle screw to pass through, the second connecting branch (20) includes a smooth through-hole (124) for receiving the head of a clamping screw whose shank is screwed into a corresponding screwthreaded hole (23) on the first connecting branch (19).

16. Spinal therapy device comprising:

vertebral anchoring elements (1, 2, 200, 202, 50, 56) having an anchoring part (9, 15, 50, 150, 56) shaped to be anchored to the bone of a vertebra and extended by a screwthreaded cylindrical part (5) onto which a clamping nut (8) is screwed, the screwthreaded cylindrical part having a base, at least one circular cross-section fastening rod (3) having a smooth outside surface, connecting slides (4) for connecting anchoring elements (1, 2, 200, 202, 50, 56) to the fastening rod (3), the connecting slides (4) having a clamping part (17) and a connecting part (18), the clamping part (17) having inside surfaces (22) shaped to surround a section of the fastening rod (3) and being deformable for selectively clamping said clamping part to and releasing said clamping part from the fastening rod (3), the connecting part (18) having a first branch (19) and a second branch (20) extending laterally and parallel to each other from two lips of a longitudinal slot (100) in the clamping part (17), said branches (19, 20) of the connecting part having corresponding through-holes (23, 124) for receiving the screwthreaded cylindrical part (5) of one of said anchoring elements for clamping the branches (19, 20) together and thereby clamping the clamping part (17), wherein:

the anchoring elements (1, 2, 200, 202, 50, 56) include a locking plate (7) with a bearing surface (12) generally perpendicular to the axis of the screwthreaded cylindrical part (5) and extending from the base of the screwthreaded cylindrical part, the bearing surface (12) of the locking plate (7) includes first non-slip projections (16), the first branch (19) of the connecting part (18) of a corresponding connecting slide (4), having a first contact surface (25) adapted to bear against the bearing surface (12) of one of said anchoring elements, includes corresponding first non-slip projections (27) to oppose any rotation and any lateral displacement of the connecting slide (4) relative to said one of said anchoring elements after clamping of the nut (8) against the opposite second contact surface (26) of the second branch (20) of the connecting part (18), wherein the connecting slide (105) is of generally parallelepiped shape, slit axially by a slot (28) having a circular cross-section first part (29) for the fastening rod (3) to pass through and a smaller cross-section second part (30) ending at an enlargement (31), the first part (29) communicating with a slot opening (32), the slot opening (32) enabling lateral insertion of the fastening rod (3) when the clamping member is released.

17. Spinal therapy device comprising:

vertebral anchoring elements (1, 2, 200, 202, 50, 56) having a longitudinal axis and having an anchoring part (9, 15, 50, 150, 56) extending along the longitudinal axis and shaped to be anchored to the bone of a vertebra and extended by a screwthreaded cylindrical part (5) onto which a clamping nut (8) is screwed, the screwthreaded cylindrical part extending along the longitudinal axis and having a base, at least one circular cross-section fastening rod (3) having a smooth outside surface, connecting slides (4) for connecting anchoring elements (1, 2, 200, 202, 50, 56) to the fastening rod (3), the connecting slides (4) having a clamping part (17) and a connecting part (18), the clamping part (17) having inside surfaces (22) shaped to surround a section of the fastening rod (3) and being deformable for selectively clamping said clamping part to and releasing said clamping part from the fastening rod (3), the connecting part (18) having a first branch (19) and a second branch (20) extending laterally and parallel to each other from two lips of a longitudinal slot (100) in the clamping part (17), said branches (19, 20) of the connecting part having corresponding through-holes (23, 124) for receiving the screwthreaded cylindrical part (5) of one of said anchoring elements for clamping the branches (19, 20) together and thereby clamping the clamping part (17), wherein:

the anchoring elements (1, 2, 200, 202, 50, 56) include a locking plate (7) with a bearing surface (12) generally perpendicular to the axis of the screwthreaded cylindrical part (5) and extending from the base of the screwthreaded cylindrical part, the bearing surface (12) of the locking plate (7) includes first non-slip projections (16), the first branch (19) of the connecting part (18) of a corresponding connecting slide (4), having a first contact surface (25) adapted to bear against the bearing surface (12) of one of said anchoring elements, includes corresponding first non-slip projections (27) to oppose any rotation and any lateral displacement of the connecting slide (4) relative to said one of said anchoring elements after clamping of the nut (8) against the opposite second contact surface (26) of the second branch (20) of the connecting part (18), wherein the first branch (19), including the first contact surface (25) adapted to bear against the bearing surface (12) of said one of the anchoring elements, is offset outwardly the relative to tan axis (II—II) of the claimping part (17), wherein the connecting slide (4) is asymmetric with respect to the axis (II—II) of the clamping part (17).

18. Device according to claim 17 wherein:

the connecting branches (19, 20) of the connecting slide (4) each include a single through-hole (23, 124), the anchoring element is a double-threaded bone screw (1), the bone screw (1) including a first screwthreaded part (5) and a coaxial second cylindrical screwthreaded part (9) on the opposite side of the locking plate (7), the second screwthreaded part (9) being adapted to be screwed into bone, wherein the anchoring element simultaneously serves as a clamping member and an anchoring member.

19. Spinal therapy device comprising:

vertebral anchoring elements (1, 2, 200, 202, 50, 56) having an anchoring part (9, 15, 50, 150, 56) shaped to be anchored to the bone of a vertebra and extended by a screwthreaded cylindrical part (5) onto which a clamping nut (8) is screwed, the screwthreaded cylindrical part having a base, at least one circular cross-section fastening rod (3) having a smooth outside surface, connecting slides (4) for connecting anchoring elements (1, 2, 200, 202, 50, 56) to the fastening rod (3), the connecting slides (4) having a clamping part (17) and a connecting part (18), the clamping part (17) having inside surfaces (22) shaped to surround a section of the fastening rod (3) and being deformable for selectively clamping said clamping part to and releasing said clamping part from the fastening rod (3), the connecting part (18) having a first branch (19) and a second branch (20) extending laterally and parallel to each other from two lips of a longitudinal slot (100) in the clamping part (17), said branches (19, 20) of the connecting part having corresponding through-holes (23, 124) for receiving the screwthreaded cylindrical part (5) of one of said anchoring elements for clamping the branches (19, 20) together and thereby clamping the clamping part (17), wherein:

the anchoring elements (1, 2, 200, 202, 50, 56) include a locking plate (7) with a bearing surface (12) generally perpendicular to the axis of the screwthreaded cylindrical part (5) and extending from the base of the screwthreaded cylindrical part, the bearing surface (12) of the locking plate (7) includes first non-slip projections (16), the first branch (19) of the connecting part (18) of a corresponding connecting slide (4), having a first contact surface (25) adapted to bear against the bearing surface (12) of one of said anchoring elements, includes corresponding first non-slip projections (27) to oppose any rotation and any lateral displacement of the connecting slide (4) relative to said one of said anchoring elements after clamping of the nut (8) against the opposite second contact surface (26) of the second branch (20) of the connecting part (18), wherein the inside surfaces (22) of the clamping part (17) have second non-slip projections (24) opposing rotation of the connecting slide (4) about the fastening rod (3) after clamping of the clamping member.

20. Device according to claim 19 wherein the second non-slip projections (24) comprise longitudinal ribs.

21. A method of treating a spinal column of a patient, the spinal column comprising a plurality of vertebrae and having an abnormal deformation, the method comprising the steps of:

anchoring a plurality of anchoring elements in vertebrae, said anchoring elements having a longitudinal axis and having a long male screwthreaded cylindrical part with a locking plate, the male screwthreaded cylindrical part extending along the longitudinal axis, each locking plate having bearing surfaces with a plurality of non-slip projections, shaping a fastening rod having a circular cross-section and a smooth outside surface to be close to a normal physiological curvature of the patient, and positioning the fastening rod in a sagittal plane of the patient, fitting connecting slides, having a clamping part and a connecting part, on said fastening rod, said connecting slide clamping parts having inside surfaces shaped to surround a section of said fastening rod, said connecting slide connecting parts having through holes for receiving said male screwthreaded cylindrical parts and having non-slip projections, inserting the male screwthreaded cylindrical parts into said slide through holes, screwing clamping nuts onto said male screwthreaded cylindrical parts, while using the non-slip projections to prevent rotation of the anchoring elements while the nuts are being tightened, and to enable adjustment of an angular position of the connecting slides on the anchoring elements before the nuts have been completely tightened, locking the anchoring elements nearest the rod, to immobilize the rod in the sagittal plane and to prevent it from rotating, and progressively tightening clamping nuts of more distant anchoring elements to reduce progressively the vertebral curvature.

* * * * *